(12) United States Patent
Flach et al.

(10) Patent No.: US 8,452,420 B2
(45) Date of Patent: May 28, 2013

(54) IMPLANTABLE CATHETER LEAD OR ELECTRODE LEAD

(75) Inventors: Erhard Flach, Berlin (DE); Tassilo Landgraf, Berlin (DE); Enlen Doce, Berlin (DE)

(73) Assignee: BIOTRONIK CRM Patent AG (CH)

( * ) Notice: Subject to any disclaimer, the term of this patent is extended or adjusted under 35 U.S.C. 154(b) by 672 days.

(21) Appl. No.: 12/510,527

(22) Filed: Jul. 28, 2009

(65) Prior Publication Data

US 2011/0029057 A1 Feb. 3, 2011

(30) Foreign Application Priority Data

Jul. 28, 2008 (DE) .......................... 10 2008 040 773

(51) Int. Cl.
*A61N 1/00* (2006.01)
*A61B 17/08* (2006.01)
(52) U.S. Cl.
USPC ............... 607/126; 607/36; 607/37; 607/128; 606/213
(58) Field of Classification Search
USPC ........................ 607/36–37, 126, 128; 606/213
See application file for complete search history.

(56) References Cited

U.S. PATENT DOCUMENTS

| 5,931,864 | A | 8/1999 | Chastain et al. |
| 5,951,597 | A | 9/1999 | Westlund et al. |
| 6,178,356 | B1 | 1/2001 | Chastain et al. |
| 6,315,790 | B1 * | 11/2001 | Gerberding et al. .......... 623/1.11 |
| 2004/0059404 | A1 | 3/2004 | Bjorklund et al. |
| 2004/0162599 | A1 | 8/2004 | Kurth |
| 2005/0065589 | A1 * | 3/2005 | Schneider et al. ............ 607/126 |
| 2006/0020317 | A1 | 1/2006 | Flach et al. |
| 2006/0030921 | A1 | 2/2006 | Chu |
| 2006/0292912 | A1 | 12/2006 | Bjorklund et al. |
| 2008/0249596 | A1 * | 10/2008 | Shiroff et al. ................. 607/126 |
| 2010/0256719 | A1 | 10/2010 | Bjorklund et al. |

FOREIGN PATENT DOCUMENTS

| DE | 10 2004 035 903 A1 | 2/2006 |
| EP | 1 618 919 A2 | 1/2006 |

OTHER PUBLICATIONS

European Search Report, EP 09 16 3984, Mar. 17, 2011.

* cited by examiner

*Primary Examiner* — Nicole F Lavert
(74) *Attorney, Agent, or Firm* — Craig A. Fieschko, Esq.; DeWitt Ross & Stevens S.C.

(57) ABSTRACT

An implantable catheter lead or electrode lead includes an elongated flexible lead body with the fixation means attached to the lead body, for the purpose of effecting fixation of the catheter lead or electrode lead in a predetermined position within a vessel or a bodily cavity of a patient. A releasable attachment is provided between the lead body and the fixation means such that an explantation of the catheter lead or electrode lead is possible after the attachment is released while the fixation means remains in place within the body of the patient.

22 Claims, 7 Drawing Sheets

IMPLANTABLE CATHETER LEAD OR ELECTRODE LEAD

FIELD OF THE INVENTION

The invention relates to an implantable catheter lead or electrode lead including an elongated flexible lead body, and including fixation means connected to the lead body to effect fixation of the lead at a predetermined position within a vessel or a body cavity of a patient.

BACKGROUND OF THE INVENTION

In this document, a "catheter lead" or "electrode lead" refers to any catheter to be affixed within the body of a human being or an animal, or any type of electrode lead for at least temporary intracorporal fixation. Examples include catheters for supplying fluids or objects into bodily cavities or vessels, or for draining fluids from these, pacemaker electrode leads, shock electrode leads, vascular stimulation leads, etc.

Many such catheter leads or electrode leads have long been known, and an extremely diverse variety of these are commercially available. When developing the technology for pacemakers and cardioveters, special attention was paid to the secure fixation of the electrode leads directly on the heart tissue to be stimulated or defibrillated, and a variety of different fixation mechanisms were developed to achieve this purpose.

Vascular electrodes, such as coronary sinus electrodes, must be very thin and flexible to allow them to be implanted in the desired target veins of the heart. These electrodes must be securely anchored in the target regions. In addition, it is also desirable from a clinical point of view for the electrodes to then be explantable (removable) at a later time. Passive fixations, such as, e.g., a distal thread, a helix, or other pre-shapings of the electrode body continue to result in dislocation rates of 10%-15%. What is advantageous about these electrodes is their subsequent explantation capability without complications. Actively affixable electrodes having a distal expansion element do provide effective acute fixation, but also tend to generate a positive-fit attachment of the electrode to the wall of the vein. As a result, they are generally no longer explantable.

SUMMARY OF THE INVENTION

A problem to be solved by the invention is to provide an improved catheter lead or electrode lead that is able to be affixed quickly and securely during implantation, and is also later explantable without great effort or repeat traumatization. This problem may be at least partially addressed by a catheter lead or electrode lead having the features set forth in the accompanying claims.

The invention is based on the idea that the electrode, after a certain period of time in which protection against dislocation by overgrowing tissue cannot yet be provided and the lead's fixation means must provide this protection, is no longer securely attached by fixation means, or the fixation means have disintegrated to such an extent that they have largely lost their fixation effect. It is then comparatively easy to remove the electrode lead from the vessel or bodily cavity without traumatization as a result of "tearing out" the fixation means. One version of the invention thus provides a releasable attachment such that explantation of the catheter lead or electrode lead is possible after release of the attachment while the fixation means remains in place within the body of the patient. In another version of the invention, elements made of resorbable foam or nonwoven material are provided as fixation means that dissolve within the body, after which explantation of the lead is also easily possible.

As an alternative the attachment may include an attachment element disintegratable by the application of energy into the lead, in particular, by the application of an electrical current, or introduction of UV radiation, light, or IR radiation. A version of the catheter lead or electrode lead with light-conducting properties, for example via embedded optical fibers, can allow for a selective application of the desired radiation in the region of placement of the fixation means, and for the disintegration of the attachment with the body of the lead, for example, in response to a UV pulse or mild heating using IR radiation. Specifically in the case of an electrode lead, which necessarily contains a lead connection between the proximal end and on or near electrodes disposed at the distal end, it is possible to also supply a voltage or a sequence of voltage pulses to the attachment point between the fixation means and the lead body, which voltage or voltage pulses disintegrate the relevant attachment means electrochemically.

In one version of the invention, the attachment has a resorbable or spontaneously-disintegrating attachment element. The material and dimensions of the attachment element can be selected here such that the resorption, disintegration or destruction results after a predetermined time span in a release of the attachment within which the catheter lead or electrode lead has been overgrown by bodily tissue to such an extent that it no longer dislocates spontaneously. The same selection of material or dimensioning principle can apply to any version of the invention in which the fixation means are designed to be resorbable or decomposable per se.

Suitable resorbable materials, or materials that decompose from the effect of bodily fluids, have long been known as surgical suturing material, and from joint and bone prosthetics, and can in principle also be employed within the invention. Included here are, for example, resorbable plastics or certain metals and their alloys, such as, for example, magnesium and Mg alloys.

In an especially simple version of the invention, the attachment has a resorbable, disintegratable or destroyable retaining ring that secures the fixation means to the lead body only in its intact initial state. This version is especially simple and inexpensive to fabricate since, first of all, suitably formed fixation means can easily be slid onto the lead body. The retaining ring is then in turn mounted on these means, and this ring presses these against the lead body as long as the body maintains its integrity. This nonpositive attachment is supported by a positive attachment between the lead body and fixation means, or can be replaced entirely by a positive attachment between the lead body, fixation means, and retaining ring.

Another version of the invention provides that the fixation means be disposed on separate ring segments that in each case enclose the lead body only section-wise (e.g., by half in the form of a half-ring), and are secured to the lead body, but following resorption, disintegration or destruction, they release from the lead body.

Another version that is especially easy to fabricate and manipulate is characterized by a spring-elastic fixation means that can be compressed into an approximately closed ring shape and in this shape can tightly surround the lead body, but in response to removal of a radially outward-directed retaining force, it snaps back into an approximately circular-segment shape and thereby releases from the lead body. A spring-elastic metal alloy (e.g., Nitinol), or also an appropriate plastic material, known as a memory-effect metal, or the like, are suitable for fabricating this type of fixation element.

In the version of the invention in which foam elements or nonwoven elements are provided as fixation means, these means are optionally composed of a material that is swellable in blood, with the result that an increase in the volume of the fixation means occurs after implantation, which volume increase can enhance the fixation effect of the fixation means. In another version, provision is made whereby the foam means or nonwoven means is or are attached by positive fit to the lead body, that is, is for example, simply clipped on there or secured by an another snap-in attachment. An adhesive-type attachment can also be considered as an alternative.

In addition to fixation means or the form of their attachment to the lead body, means for effecting the temporary deactivation of the attachment means are also provided in various possible versions of the invention. For example, advantageously controllable deactivation means may be provided for the catheter lead or electrode lead, which deactivation means keep the fixation means inactive during an implantation but which, after correct placement of the end of the lead, bring about immediate fixation thereof. Here the deactivation means are controllable by the operator from a proximal end of the lead so as to activate the fixation means. In another preferred version, the deactivation means have a protective sleeve that can be slid in the longitudinal direction of the lead body and/or that can be rotated about a longitudinal axis of the lead body, which sleeve can be optionally provided with incorporated recesses to accommodate the fixation means in the inactive state.

Such a version of the invention is useful for clinical use so that the anchored state of the catheter lead or electrode lead is easily detectable from outside the body. To accomplish this, the lead body and/or the fixation means and/or the attachment element have an x-ray marker that is designed to make the activation state of the fixation means detectable externally by an x-ray image of the implanted lead. The use of x-ray markers for catheter lead or electrode leads has been known for some time, and these can be employed within the invention, for example, in the form of metal rings to mark the attachment point between the fixation means and the lead body; through the metallic design of the fixation means itself; through a metallic marking of the above-referenced protective sleeve that keeps the fixation means inactive during the implantation; etc.

In another version of the invention, the fixation means are disposed at a distance from the distal end of the lead. As a result, it becomes possible, for example, to anchor an electrode line projecting by its distal end into a vessel both at one entrance or one wall of the vessel, but not within the vessel itself, and thus preclude a disturbance the blood flow by the fixation means or an unwanted proliferation of the vessel by tissue growing around the fixation means.

In another version of the invention, the fixation means have a spreading element that is expandable by the lead body or that is self-expanding in response to activation of the fixation means. This can involve a single anchor-like element; however, what is preferred is an version in which the fixation means has a group of spreading elements that are distributed in particular around the circumference of the lead body, and that surround this body in particular in a funnel-shape, calyx-shape, or tulip-shape when in the activated state. Such a group of fixation means generally provides a secure foothold for the electrode lead until the time of ingrowth, and also places less stringent demands on the skill of the operator.

In another advantageous version of the invention, the self-expanding spreading element, or the group of spreading elements, is designed as a metal component elastically pretensioned in the active state, in particular, one composed of Nitinol or a similarly effective metal alloy. In addition, it is useful if each spreading element is designed in a spade shape, plate shape, coil shape, spiral shape, or helical shape, or has correspondingly designed ends, in order to reduce trauma to the body cavity or vascular wall during fixation.

BRIEF DESCRIPTION OF THE DRAWINGS

Other advantages and useful aspects of the invention are revealed in the following description of exemplary versions based on the figures. Here.

DETAILED DESCRIPTION OF THE INVENTION

Figure 1:
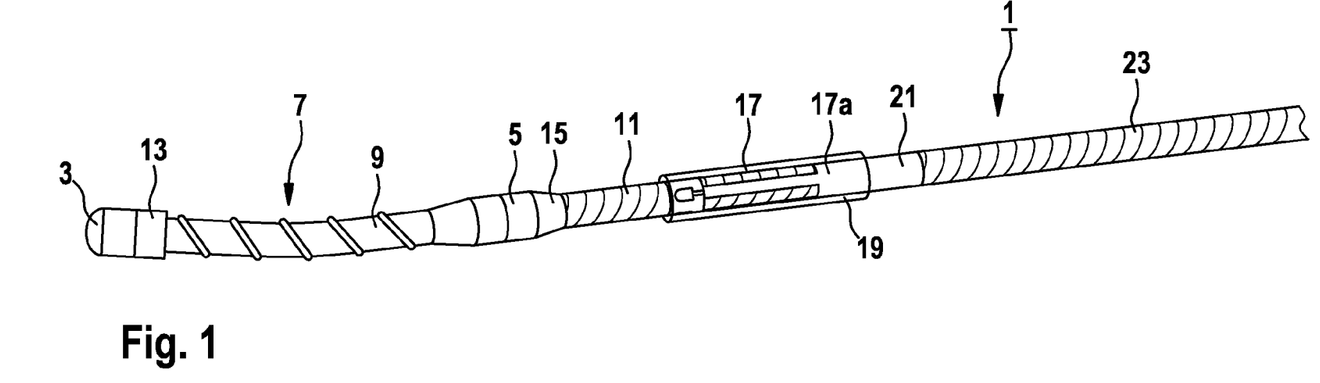
FIG. 1 is a first view of a stimulation electrode based on one version of the invention (with deactivated fixation means)
Figure 2:
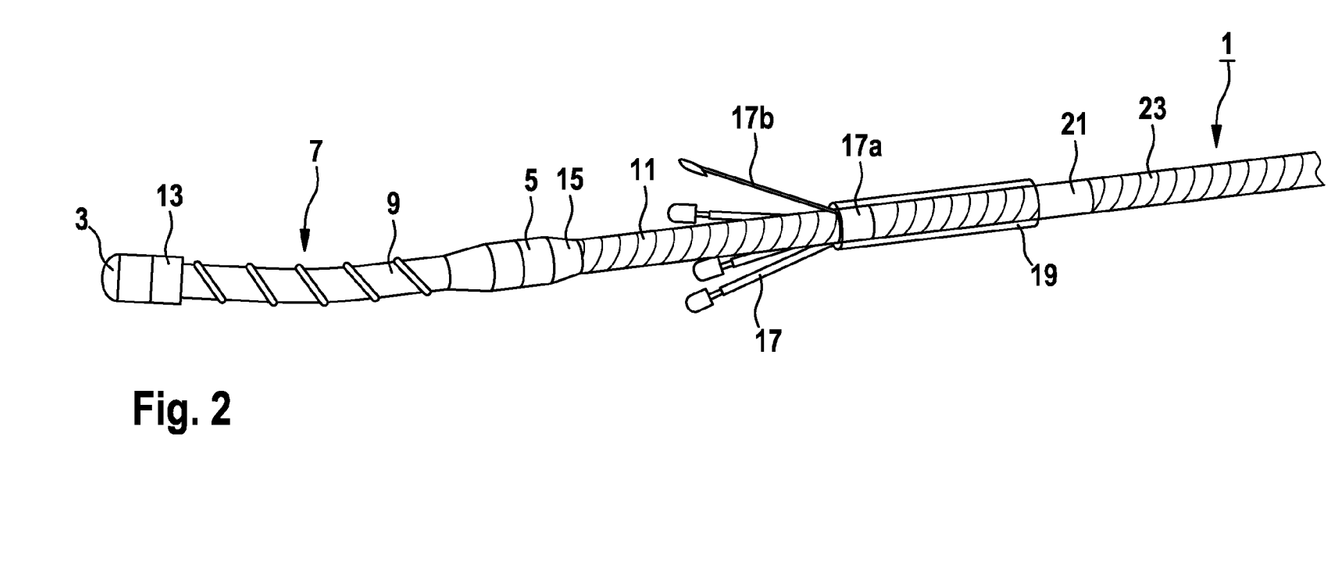
FIG. 2 is another view of the electrode lead in FIG. 1 (with activated fixation means)

FIGS. 1 and 2 illustrate the distal section of a pacemaker electrode lead 1 having a tip electrode 3 disposed at the distal end, and a ring electrode 5 spaced a certain distance therefrom on a flexible plastic lead body 7 that can be composed, for example, of silicon tube with a Parylene coating which can enhance the sliding properties. Coiled electrode leads 9 and 11 run within lead body 7, and x-ray markers 13 and 15 are provided at the sites of tip electrode 3 and the ring electrode 5. In a preferred version, electrodes 3 and 5 can themselves be designed as x-ray markers.

A spreading element 17 composed of Nitinol is clamped onto lead body 7, which body in the inactive state shown in FIG. 1 is held by a tubular sleeve 19 that has a platinum stop ring 21 and is slipped from the proximal end of electrode lead 1 over this lead. These are mounted on the front (distal) end of a polyurethane (PU) tube 23 that has a slip-type coating. In this state, the pacemaker electrode lead 1 can be inserted with low resistance into the body of the patient.

In the state shown in FIG. 2, PU tube 23 with tubular sleeve 19 attached therein has been somewhat retracted, while spreading element 17 has expanded and is now in the active state for fixation of electrode lead 1. In the version shown in FIGS. 1 and 2, the element includes four arms 17b spreading out in a funnel shape from a platinum clamping ring 17a, the ends of the arms 17b being designed in a widened spade-like shape to reduce trauma to the bodily tissue contacted by them. The spreading element 17 can be attached to the electrode 1 temporarily. After disintegration of the attachment, the spreading element 17 releases from the lead body 7 and thus becomes inactive. After the fixation has become inactive, the lead body 7 is held only by tissue that has in the mean time grown around it, and electrode lead 1 thus can then be explanted if necessary without significantly traumatizing the surrounding bodily tissue.

Figure 3A:
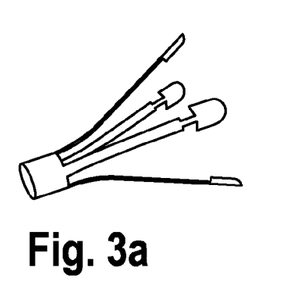
FIGS. 3a through 3h are views of various versions of fixation means for the stimulation electrode lead.
Figure 3B:
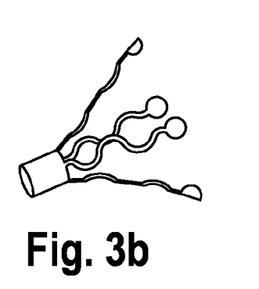
Figure 3C:
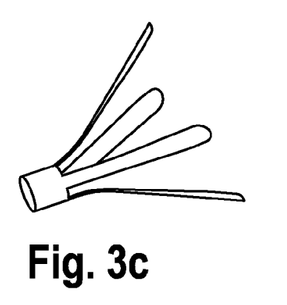
Figure 3D:
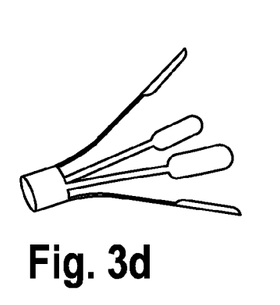
Figure 3E:
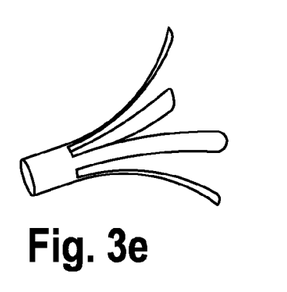
Figure 3F:
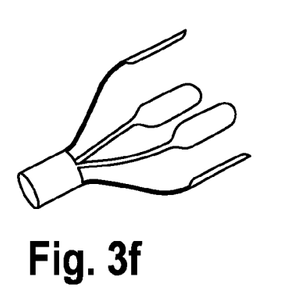
Figure 3G:
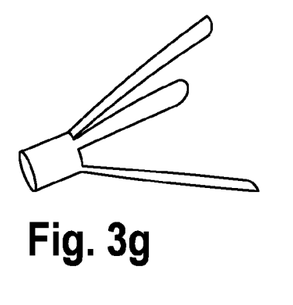
Figure 3H:
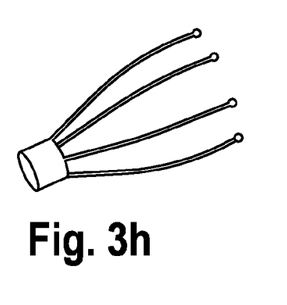

FIGS. 3a through 3h illustrate various versions of spreading elements or fixation means of a type shown for spreading element 17 of FIGS. 1 and 2. These diagrams are essentially self-explanatory such that no additional verbal description is necessary. It should simply be pointed out that the plurality of individual spreading arms of the illustrated spreading elements can describe various circumferential forms—aside from the funnel shape (FIGS. 3a through 3d and 3g), also a calyx shape (FIG. 3e) or tulip shapes (FIGS. 3f and 3h). Among the many commercially available designs, the operator can easily make a selection that is optimally matched to a catheter lead or electrode lead to be implanted in terms of a fixation that is reliable and at the same time causes as little trauma as possible.

Figure 4:
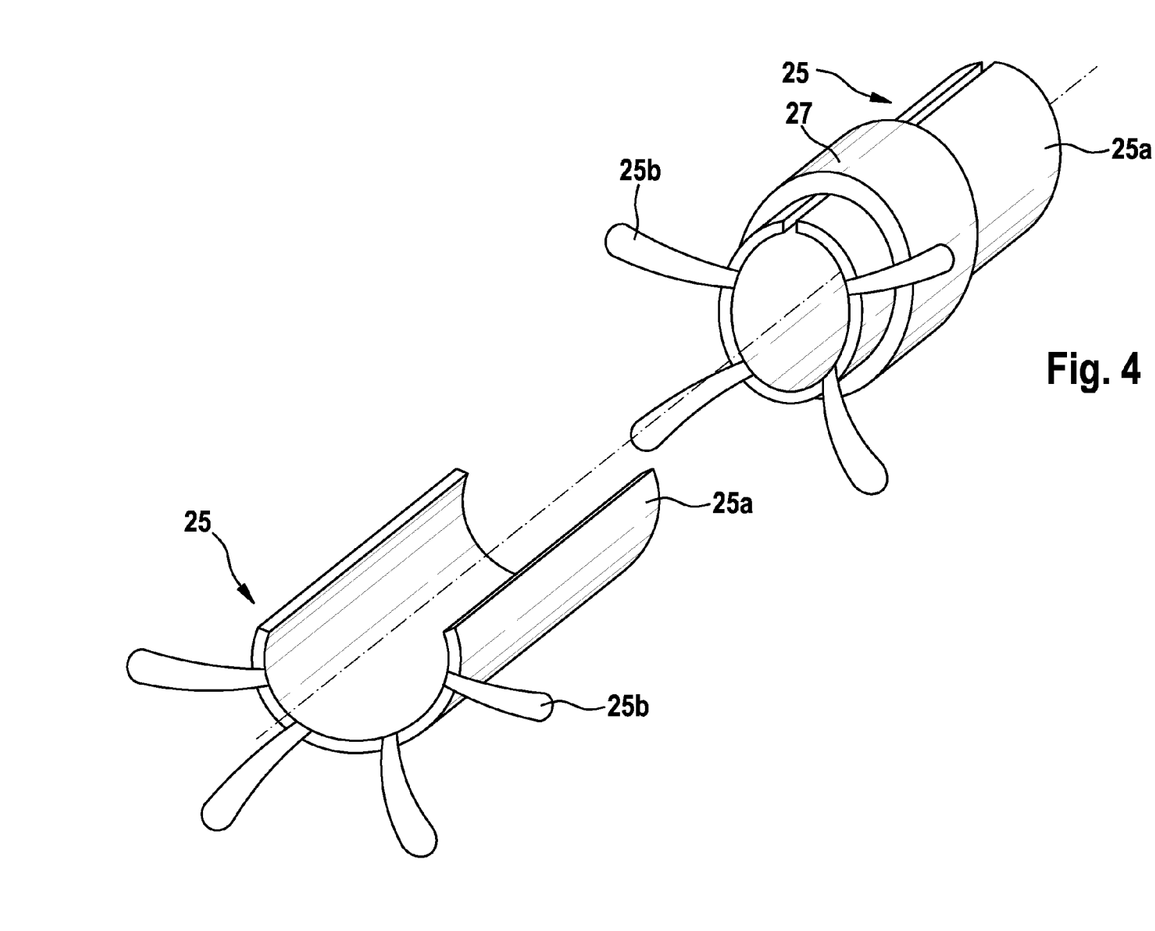
FIG. 4 is a schematic diagram showing the interaction of fixation means and a disintegratable retaining ring in another version of the catheter lead or electrode lead.

The operating principle of a preferred version of the invention is illustrated especially clearly by FIG. 4. The figure shows a spring-elastically deformable fixation means 25 having a ring segment 25a and four spreading arms 25b, first, in the untensioned state that the element takes before clamping onto a lead body (not illustrated) and after release from this body (at bottom left), and second, in ring-like closed state in which it is held by a retaining ring 27 on a lead body (at top right). In this example, the fixation element 25 can be fabricated, for example, out of Nitinol or a similarly effective material. It is also conceivable for the fixation element 25 to be a plastic having spring-elastic properties.

The ring segment or collar 25a of fixation element 25 is thus opened widely in the untensioned state and is then closed on a lead body during installation, thereby coming under tension. In this state, retaining ring 27 is slid over collar 25a, thereby preventing the fixation element 25 from re-opening. Since the ring 27 is fabricated out of a resorbable material, the fixation element 25 can then release itself from the lead body after disintegration of the material by springing back to its original, approximately semicircular shape.

Possible suitable resorbable materials for the retaining ring 27 include polyactides or other body-compatible plastics or magnesium or other body-compatible or resorbable/disintegratable metal; resorbable sutures or suture material can in principle also be considered for this purpose. In the case of certain materials—magnesium, for example—a targeted electrochemical destruction can be considered which is effected by an application of electrical current that has been appropriately selected in terms of the voltage-sensitivity or electrical-current sensitivity of the adjacent organs of the body.

The appropriate time period until resorption or disintegration of the retaining ring 27, and thus until the attachment between the lead body and the fixation element 25 is released, can be preset through a suitable selection of the material (for example, selection of the degree of polymerization and of the specific compound of the polymer, or selection of an appropriate metal alloy) and through the dimensions (in particular, wall thickness) of the ring 27. Based on available clinical experience, the fixation 25 should release after 2-3 weeks from the lead body since the electrode lead will by then usually be stabilized sufficiently by the surrounding growth of tissue that it no longer dislocates spontaneously.

Figure 5A:
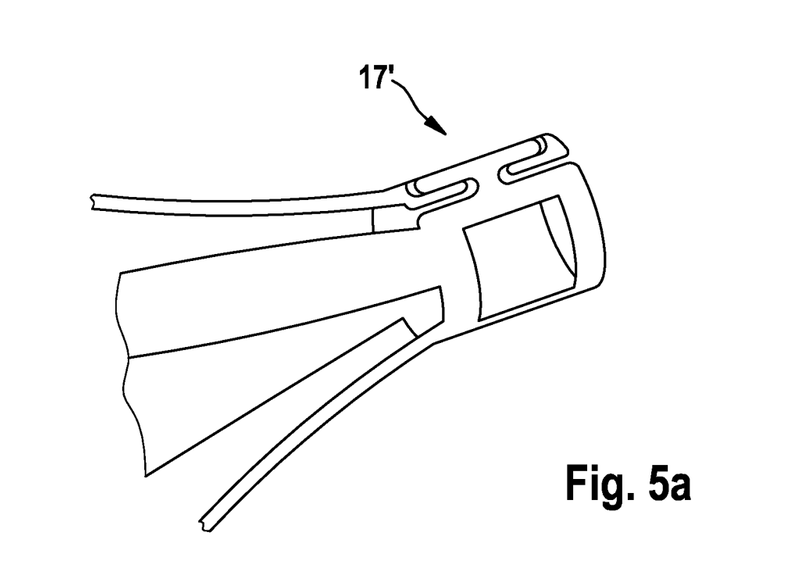
FIGS. 5a and 5b provide detailed views of specific versions of the attachment region between fixation means and lead body.
Figure 5B:
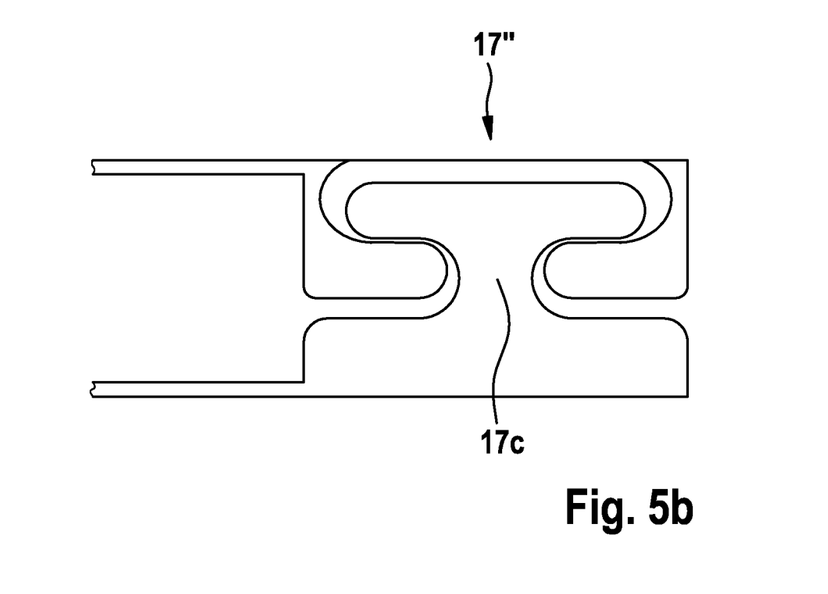

FIGS. 5a and 5b illustrate modified spreading elements 17' and 17", the ring segment of which is spring-elastically designed for attachment to a lead body and has recesses to create a combined nonpositive and positive fit between the spreading element and the lead body (FIG. 5a), or a clasp 17c (FIG. 5b) that closes in response to radial pressure and then self-locks.

FIGS. 6a through 6f have schematic diagrams illustrating other versions for electrode leads having elastically deformable foam elements, both during implantation and after activation. Following the reference numbers used in illustrating and describing the first version of the invention, in all versions of FIGS. 6a through 6f, an electrode lead is shown by number 31, a tip electrode is shown by number 33, a ring electrode is shown by number 35, and a flexible plastic lead body is shown by number 37.

Figure 6A:
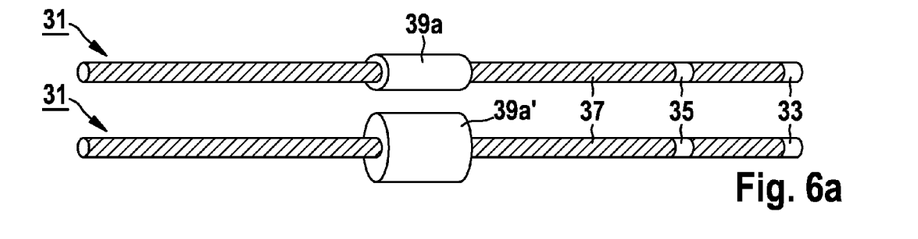
FIGS. 6a through 6f are schematic diagrams of alternative versions of electrode leads.

FIG. 6a illustrates two versions of the electrode lead 31, each having an annular foam fixation element 39a or 39a' provided in the proximal direction spaced a distance from ring electrode 35 on lead body 37, wherein the fixation element 39d differs from the element 39a in terms of its greater diameter.

Figure 6B:
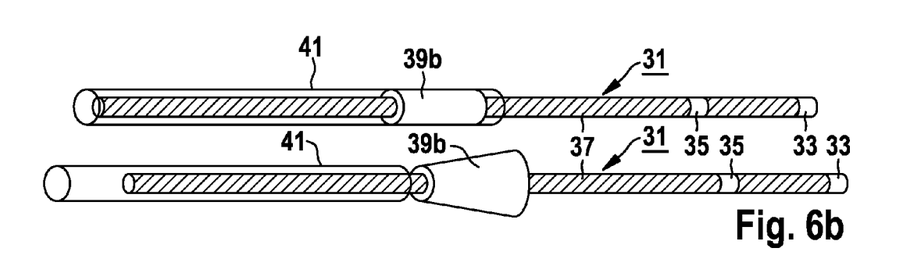
Figure 6C:
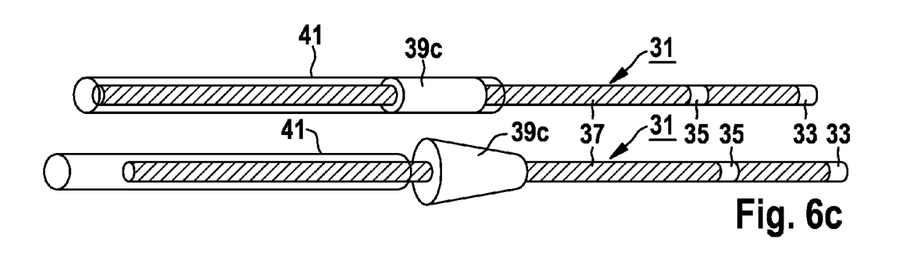

In the versions of electrode lead 31 of FIGS. 6b and 6c, in each case a truncated-cone-shaped foam fixation ring 39b (FIG. 6b) and 39c (FIG. 6c) is provided, wherein the orientation of each cone is reversed in the two versions. What is illustrated in both figures (as well as in the following figures) is in each case the state during implantation of the electrode lead, that is, with the silicon tube 41 slid over the fixation element and making this element inactive, or after implantation, that is, with retracted silicon tube and fully expanded, and thus active, fixation element.

Figure 6D:
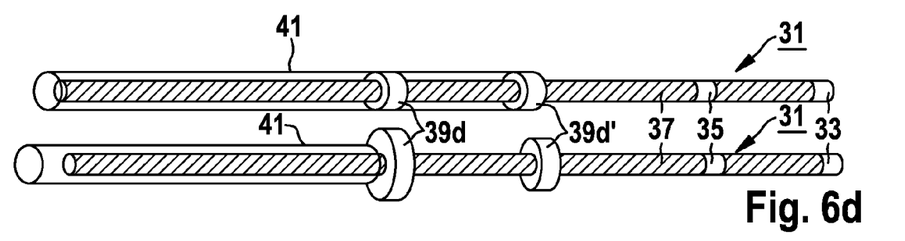

FIG. 6d illustrates another version of the electrode lead including two fixation rings 39d and 39d' spaced apart and of differing diameter and relatively low height, both of which are placed proximally relative to ring electrode 35.

Figure 6E:
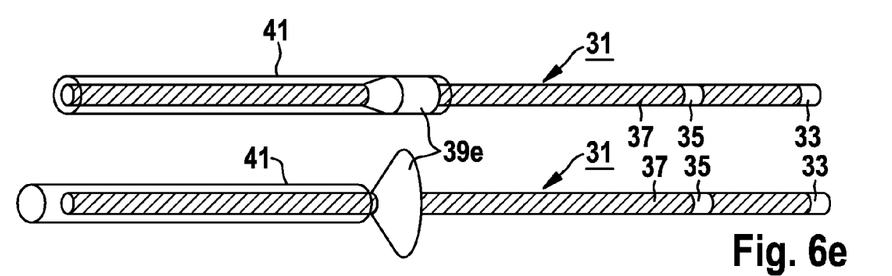
Figure 6F:
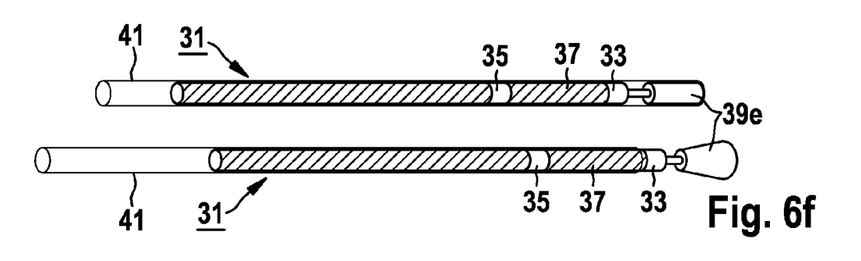

As a further modification, FIG. 6e illustrates a mushroom-like or hood-shaped foam fixation element 39e that, as in the versions described above, is mounted on the electrode lead (preferably by positive fit) proximally relative to ring electrode 35. Finally, FIG. 6f illustrates an version that is fundamentally different in terms of the placement of the fixation means: Here a truncated-cone-shaped fixation element 39f, the diameter of which expands into an untensioned and thus activated state, is located on the distal end of electrode lead 31, that is, still beyond tip electrode 33.

The foam element or nonwoven element can vary in its dimensions and its shape: They can, for example, be shaped so as to be conical, oval, square, spherical, and the like. The foam and all of the components participating in the fixation are resorbable, e.g., composed of polyurethane, polylactate, polyglycol (polyethylene glycol), gelatins, collagens, or of tamponades used to arrest bleeding, such as, e.g., GELA-SPON®. The fixation is completely reabsorbed within a defined time period that can be adjusted as a function of the foam type, density, or thickness. The foam or nonwoven material can be provided with coagulation-modifying means or other agents.

Both for an implantation procedure and also any explantation procedure, observation from outside the body through x-ray imaging is desirable.

Figure 7A:
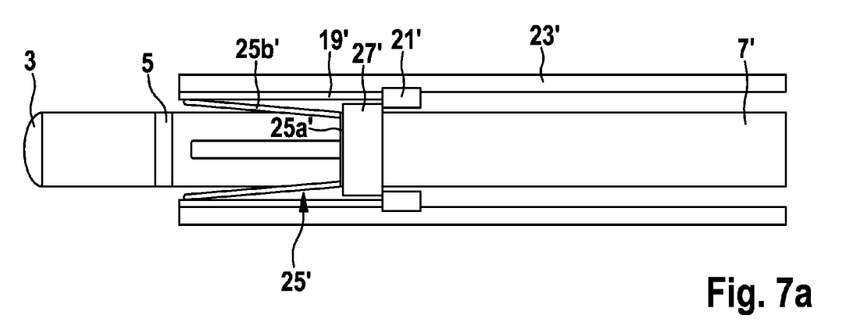
FIGS. 7a through 7c schematically illustrate the active and inactive states of the fixation means and the position of the x-ray-visible markings.
Figure 7B:
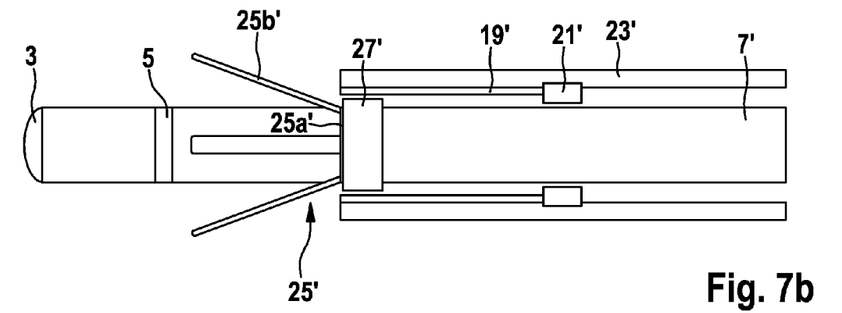
Figure 7C:
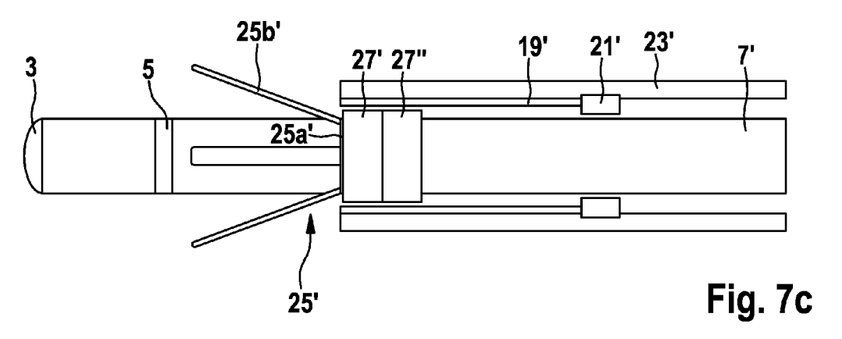

FIGS. 7a through 7c illustrate by way of example the position of the x-ray markers, by means of which an operator can recognize whether the fixation means are inactive or active. FIG. 7a thus illustrates an electrode lead having an x-ray-visible tip electrode 3 and ring electrode 5, as well as a fixation element 25'. The fixation element 25' is not visible to x-rays. Fixation element 25' is affixed to the electrode lead by retaining ring 27'. Retaining ring 27' on clamping ring 25a' is designed to be x-ray-visible by selecting an appropriate material. In another version, retaining ring 17' is designed to be biodegradable, for example, as described above composed of a biodegradable metal or plastic. In this case the x-ray visibility is created by the admixture of x-ray-visible materials, such as, for example, gold dust. In an version shown in FIG. 7c, a marker ring 27" can be provided in addition to biodegradable retaining ring 27' that in this case does not have to be x-ray-visible. The marker ring 27" then does not cover clamping ring 25a' of the fixation element.

In FIG. 7a, what is shown (with reference to the description of FIG. 1) is the electrode lead in a state in which the lead can be implanted into the body, that is, such that the tubular sleeve 19' attached to PU tube 23' keeps the fixation element inactive. Stop ring 21'; which delimits tubular sleeve 19' against PU tube 23' and secures this tube, is fabricated in this exemplary version out of an x-ray-visible material, for example, gold or platinum.

In order to enable the operator to recognize whether the fixation is in an active state attached within the vessel or inactive state, he/she can utilize an x-ray image or fluoroscopy. What is important here is the position of tip electrode 3 and of x-ray markers (metal rings) 13 and 15 identifying ring electrode 5, or the automatically x-ray-visible electrodes 3 and 5, on the one hand, and the relative position of x-ray-visible retaining ring 27' and of stop ring 21'.

Upon insertion of the electrode lead when the electrode is moved to the implantation site and fixation element 25' is in the inactive position, stop ring 21' immediately strikes retaining ring 27'. If the operator consults the x-ray image, he/she will recognize three clear marker signals in the x-ray image: from the tip electrode and ring electrode 3 and 5 (or associated x-ray markers 13 and 15), and a signal from immediately adjacent retaining ring 27' and stop ring 21'. This state is illustrated in FIG. 7a.

At the implantation site, the operator can activate fixation element 25' and thereby attach the electrode by means of expandable arms 25b' by retracting PU tube 23' in the proximal direction. In response to this motion, x-ray-visible stop ring 21' moves away from x-ray-visible retaining ring 27' in the proximal direction. As a result, four clear marker signals are now visible in the x-ray image: two signals for electrodes 2 and 5 (or associated x-ray markers 13 and 15) and one signal each for retaining ring 27' and stop ring 21'. This indicates to the operator that fixation element 27' has been released. This state is shown in FIG. 7b.

FIG. 7c illustrates the state of activated fixation element 25' with a separate marker ring 27", wherein here too four marker signals are detectable in an x-ray image.

Repositioning is also possible in the event of a faulty positioning of the electrode lead whereby PU tube 23' is again slid in the distal direction such that fixation element 25' becomes inactive. The inactive position, in which the physician can reposition the electrode lead without risk to the patient, is recognized by the operator based on the condition that again only three marker signals are detectable in the x-ray image.

The version of the invention is not restricted to the above-described examples and highlighted aspects; instead, a variety of modifications is possible that are within the contemplation of a person skilled in the art. It will be apparent to those skilled in the art that numerous modifications and variations of the described examples and versions are possible in light of the above teaching. The disclosed examples and versions are presented for purposes of illustration only. Therefore, it is the intent to cover all such modifications and alternate versions as may come within the scope of this invention.

What is claimed is:

1. An implantable lead for a catheter and/or an electrode, the lead including:
   a. an elongated flexible lead body,
   b. fixation means releasably attached to the lead body for:
      (1) having one or more portions of the fixation means move from an initial location nearer the lead body to a deployed location spaced from the lead body, with the deployed portions fixing the lead body in a predetermined position within a vessel or a bodily cavity of a patient, and
      (2) releasing from the lead body such that the lead body is removable from the vessel or the bodily cavity of the patient while the fixation means remains fixed in the predetermined position within the vessel or the bodily cavity of the patient.

2. The lead of claim 1 wherein:
   a. the moving portions of the fixation means are defined by elongated members spaced around a circumference of the lead body, and
   b. each member has:
      (1) a first end of the member's length situated nearer the lead body, and
      (2) a second end of the member's length spaced from the lead body, when in the deployed location.

3. The lead of claim 1 wherein:
   a. the fixation means circumferentially encircles the lead body, and
   b. the entirety of an outer circumference of the fixation means moves from the initial location nearer the lead body to the deployed location spaced from the lead body.

4. The lead of claim 1 wherein the fixation means includes an attachment to the lead body wherein the attachment destructs to release the fixation means from the lead body.

5. The lead of claim 4 wherein the fixation means, as well as the attachment, destructs to release the fixation means from the lead body.

6. The lead of claim 4 wherein the attachment destructs in response to the application of energy to the lead body.

7. The lead of claim 4 wherein the attachment destructs in response to the application of one or more of:
   a. electric current,
   b. light having one or more wavelengths between and/or within the ultraviolet and infrared spectral ranges.

8. The lead of claim 4 wherein the attachment includes a retaining ring at least partially fit about the lead body.

9. The lead of claim 1 wherein:
   a. the fixation means includes an attachment to the lead body, the attachment including a retaining ring at least partially fit about the lead body;
   b. the fixation means includes one or more elongated members, each elongated member having:
      (1) a first end of the member's length situated nearer the lead body and the retaining ring, and
      (2) a second end of the member's length spaced from the lead body and the retaining ring.

10. The lead of claim 1:
    a. wherein the fixation means are situated on ring segments, each ring segment extending about a portion of a circumference of the lead body;
    b. further including an attachment securing the ring segments about the lead body, wherein the attachment destructs to release the ring segments from the lead body.

11. The lead of claim 1 wherein at least one of:
    a. the lead body, and
    b. the fixation means,
    includes an x-ray marker.

12. The lead of claim 1:
    a. further including a sleeve about the lead body, the sleeve holding the fixation means in an initial location nearer the lead body, and
    b. wherein moving the sleeve about the lead body moves the fixation means to a deployed location spaced from the lead body.

13. The lead of claim 1:
   a. wherein the fixation means elastically deploys to a deployed location spaced from the lead body unless the fixation means is restrained against deployment;
   b. further including a sleeve fit about the lead body and the fixation means, the sleeve restraining the fixation means in an initial location nearer the lead body.

14. An implantable lead for a catheter and/or an electrode, the lead including:
   a. an elongated flexible lead body, and
   b. a fixator situated about at least a portion of a circumference of the lead body, wherein at least a portion of the fixator:
      (1) deploys circumferentially outwardly from the lead body, thereby engaging the walls of a vessel or cavity wherein the lead body and fixator are inserted;
      (2) is releasable from the lead body after deployment by falling from the circumference of the lead body, whereby release of the fixator from the lead body allows withdrawal of the lead body from any vessel or cavity wherein the lead body and fixator are inserted, without interference from the fixator.

15. The implantable lead of claim 14 wherein the fixator includes an attachment to the lead body wherein the attachment destructs to release the fixator from the lead body.

16. The implantable lead of claim 14 wherein the fixator includes an attachment to the lead body, the attachment including a retaining ring at least partially fit about the lead body.

17. The implantable lead of claim 16 wherein the fixator includes one or more elongated members, each having:
   a. a first end of the member's length situated nearer the lead body and the retaining ring, and
   b. a second end of the member's length spaced from the lead body and the retaining ring.

18. The implantable lead of claim 14 wherein:
   a. the fixator extends about the entirety of the circumference of the lead body; and
   b. the entirety of an outer circumference of the fixator deploys circumferentially outwardly from the lead body.

19. An implantable lead for a catheter and/or an electrode, the lead including:
   a. an elongated flexible lead body,
   b. a fixator situated on the lead body, the fixator:
      (1) being movable between:
         (a) an undeployed state wherein one or more deployable portions of the fixator are situated in an initial location nearer an outer circumference of the lead body, and
         (b) a deployed state wherein the deployable portions are situated in a deployed location radially spaced from the outer circumference of the lead body,
         wherein the lead body is adapted, when situated within a human body, to have the fixator deployed to engage the human body, and thereby engage the lead body to the human body;
      (2) including an attachment to the lead body wherein the attachment destructs to release the fixator from the lead body, thereby allowing the lead body to be removed from the human body without interference from the fixator.

20. The implantable lead of claim 19 wherein the attachment to the lead body:
   a. extends about at least a portion of the outer circumference of the lead body, and
   b. is at least partially formed of material which is resorbable or decomposable within the human body.

21. The implantable lead of claim 19 wherein the attachment to the lead body includes a retaining ring.

22. The implantable lead of claim 19 wherein the fixator is at least partially formed of material which is resorbable or decomposable within the human body.

* * * * *